US010842732B2

(12) United States Patent
Barrie

(10) Patent No.: US 10,842,732 B2
(45) Date of Patent: Nov. 24, 2020

(54) SHELLAC BASED SKIN CARE LOTION

(71) Applicant: Mantrose-Haeuser Co., Inc., Westport, CT (US)

(72) Inventor: William E. Barrie, Fairfield, CT (US)

(73) Assignee: MANTROSE-HAEUSER CO., INC., Lincoln, RI (US)

( * ) Notice: Subject to any disclaimer, the term of this patent is extended or adjusted under 35 U.S.C. 154(b) by 125 days.

(21) Appl. No.: 14/639,408

(22) Filed: Mar. 5, 2015

(65) Prior Publication Data

US 2015/0258010 A1 Sep. 17, 2015

Related U.S. Application Data

(60) Provisional application No. 61/954,150, filed on Mar. 17, 2014.

(51) Int. Cl.
| | | |
|---|---|---|
| *A61K 36/00* | (2006.01) | |
| *A61K 8/92* | (2006.01) | |
| *A61Q 19/00* | (2006.01) | |
| *A61K 8/06* | (2006.01) | |

(52) U.S. Cl.
CPC .............. *A61K 8/927* (2013.01); *A61K 8/062* (2013.01); *A61Q 19/00* (2013.01); *A61K 2800/49* (2013.01)

(58) Field of Classification Search
None
See application file for complete search history.

(56) References Cited

U.S. PATENT DOCUMENTS

| | | | |
|---|---|---|---|
| 5,053,218 A | 10/1991 | Shernov | |
| 6,348,217 B1 | 2/2002 | Santos et al. | |
| 6,551,606 B1 * | 4/2003 | Golz-Berner | A61K 8/345 424/401 |
| 2002/0164362 A1 * | 11/2002 | Golz-Berner | A61K 8/042 424/401 |
| 2006/0188465 A1 * | 8/2006 | Perrier | A61K 8/73 424/70.13 |
| 2010/0297043 A1 | 11/2010 | Lowndes et al. | |

FOREIGN PATENT DOCUMENTS

| | | |
|---|---|---|
| CN | 1261268 A | 7/2000 |
| CN | 103013339 A | 4/2013 |
| CN | 1261268 A | 3/2020 |
| JP | 2002509548 A | 3/2002 |
| WO | WO-9906011 A2 * | 2/1999 ............ A61K 8/042 |
| WO | WO-9906488 A1 * | 2/1999 ............ A61K 8/927 |
| WO | 2013039826 A1 | 3/2013 |

OTHER PUBLICATIONS

International Search Report and Written Opinion from International Application No. PCT/US2015/18853 dated May 20, 2015.
Search Report for European Patent Application No. 15764271.1 dated Sep. 27, 2017.
English Text of First Notification of Office Action for Chinese Patent Application No. 201580012510.3 dated Sep. 28, 2018.
Response to Search Report for European Patent Application No. 15764271.1 dated May 3, 2018.
Examination Report for European Patent Application No. 15764271.1 dated Oct. 5, 2018.
First Office Action for Israeli Patent Application No. 247633 dated Nov. 29, 2018.
Response to Office Action dated Oct. 5, 2018 for European Patent Application No. 15764271.1 dated Mar. 25, 2019.
Notice of Reasons for Rejection for Japanese Patent Application No. 2016-556979 dated Jan. 7, 2019.
Second Written Opinion for Singapore Patent Application No. 11201607682X dated Nov. 5, 2018.
Second Notification of Office Action for Chinese Patent Application No. 201580012510.3 dated Jul. 9, 2019.
Examination Report No. 1 for Australian Patent Application No. 2015231854 dated May 7, 2019.
Response to Examination Report No. 1 for Australian Patent Application No. 2015231854 dated May 20, 2019.
Response to Written Opinion from Singapore Patent Application No. 11201607682X dated Apr. 5, 2019.
Response to communication dated Jul. 31, 2019 in European Patent Application No. 1576427.1 dated Oct. 29, 2019.
Communication for European Patent Application No. 15764271.1 dated Mar. 20, 2020.
Response to Office Action dated Oct. 31, 2019 for Israeli Patent Application No. 247633 dated Oct. 18, 2019.
Office Action dated Oct. 3, 2019 for Israeli Patent Application No. 247633.
Pre-Appeal Examination Report for Japanese Patent Application No. 2016-556979 dated Feb. 26, 2020.
Notice of Final Rejection for Japanese Patent Application No. 2016-556979 dated Aug. 8, 2019.
Third Office Action for Chinese Patent Application No. 201580012510.3 dated Mar. 25, 2020.
Written Opinion from Singapore Application No. 11201607682X dated Sep. 2, 2020 (6 pages).

* cited by examiner

*Primary Examiner* — Russell G Fiebig

(74) *Attorney, Agent, or Firm* — Calfee, Halter & Griswold LLP

(57) ABSTRACT

The moisturizing properties of a water-based moisturizing composition containing one or more emollients emulsified in an aqueous carrier liquid are improved by including a water-soluble shellac in the composition.

17 Claims, No Drawings

SHELLAC BASED SKIN CARE LOTION

CROSS-REFERENCE TO RELATED APPLICATION

This application claims priority to and the benefit of U.S. Provisional Patent Application Ser. No. 61/954,150, entitled "SHELLAC BASED SKIN CARE LOTION" and filed Mar. 17, 2014, the entire disclosure of which is incorporated herein by reference.

FIELD OF THE INVENTION

This invention relates to water-based skin care compositions, especially water-based skin care lotions.

BACKGROUND

Moisturizing lotions, pastes, creams and gels are well-known consumer products composed of complex mixtures of chemical agents especially designed to make the external layers of the skin (epidermis) softer and more pliable. Normally, they are water-based compositions in the form of oil-in-water emulsions in which various beneficial ingredients such as naturally occurring skin lipids and sterols, natural and/or artificial oils, humectants, emollients, lubricants and so forth are emulsified in water. When applied to the skin, they may form protective coatings which reduce the rate at which water evaporates from the skin's surface, thereby increasing the skin's hydration (water content).

Two commonly accepted techniques for measuring the effectiveness on the skin of a moisturizing composition relate to electroconductivity and transdermal water loss. In an electroconductivity test, the impedance of the surface of skin treated with the composition is determined by a suitable analytical instrument such as, for example, a Nova Dermal Phase Meter, Model DPM 9003, available from Nova Technology Corporation of Gloucester, Mass. A lower impedance (higher electroconductivity) connotes a greater concentration of retained water in the skin, thereby indicating a greater degree of moisturizing.

Transepidermal water loss or "TEWL" refers to the quantity of water that naturally passes from inside a body (animal or plant) through the epidermal layer (skin) to the surrounding atmosphere via diffusion and evaporation. In a transdermal water loss test, the rate at which water vapor is lost from the body through the skin is measured by sophisticated analytical equipment such as a DermaLab Computerized Evaporimeter, available from Cyberderm, Inc. of Broomall, Pa. A reduction in TEWL, i.e., a reduction in the rate of water vapor loss, generally connotes proportionately greater moisture barrier properties in the protective film formed by the moisturizing composition.

Although currently available moisturizing compositions work well, it is always desirable to provide improved moisturizing compositions exhibiting even better properties than available in the past.

SUMMARY OF THE INVENTION

In accordance with this invention, it has been found that water-based moisturizing compositions exhibiting improved moisturizing properties can be produced by including a small but suitable amount of a water-soluble shellac or analog in the composition. In particular, it has been found that water-based moisturizing compositions which contain a small but suitable amount of a water-soluble shellac or analog dissolved in the aqueous phase of the composition exhibit significantly improved barrier film properties, as determined by conventional electroconductivity and transdermal water loss tests.

Thus, this invention provides a water-based moisturizing composition comprising an oil in water emulsion having an aqueous phase and an oil phase emulsified in the aqueous phase, wherein the oil phase comprises one or more emollients, and further wherein the composition contains a water-soluble shellac or analog in an amount sufficient to improve the moisturizing properties of the composition.

In addition, this invention further provides a process for improving the moisturizing properties of a pre-existing moisturizing composition comprising an oil in water emulsion having an aqueous phase and an oil phase emulsified in the aqueous phase, wherein the oil phase comprises one or more emollients, the process comprising adding to the pre-existing moisturizing composition, or to one or more ingredients forming this pre-existing moisturizing composition, a water-soluble shellac or analog in an amount sufficient to improve the moisturizing properties of the pre-existing moisturizing composition.

Still further, this invention also provides a water-based moisturizing composition comprising an oil in water emulsion having an aqueous phase and an oil phase emulsified in the aqueous phase, wherein the oil phase comprises one or more emollients, and further wherein the aqueous phase comprises at least about 1 wt. %, based on the weight of the aqueous phase, of a water-soluble shellac dissolved therein.

DETAILED DESCRIPTION

Basis Weight

Unless otherwise indicated, the concentrations of ingredients specified below are given in terms of the weight of the ingredient based on the weight of the inventive moisturizing composition as a whole (or the weight of the aqueous phase of this composition if so specified) but excluding any propellant that might be present. That is to say, in those embodiments of this invention in which the inventive moisturizing composition is provided in the form of a sprayable composition in an aerosol container, the concentration of ingredients of this composition, as described below, will be understood to exclude any propellant that may also be present in the container.

Non-Sprayable Compositions

As indicated above, the inventive moisturizing compositions can be provided in the form of sprayable compositions, if desired. So, for example, the inventive moisturizing compositions of these embodiments can be delivered from non-aerosol mechanical pump spray devices or from pressurized aerosol canisters using a propellant.

Most commonly, however, the inventive moisturizing compositions will take the form of non-sprayable compositions, i.e., compositions which are too viscous to be conveniently sprayed from conventional mechanical pump sprayers or conventional pressurized aerosol canisters. Specific examples include lotions, pastes, creams and gels.

Water-Based Moisturizing Compositions

The inventive moisturizing skin care compositions are water-based. In this context, "water-based" means that the compositions are in the form of oil-in-water emulsions in which the aqueous phase constitutes the external phase of the emulsion.

It is already known to include shellac in various types of topical pharmaceutical compositions such as sunscreens and the like. See, for example, commonly assigned WO 2013/

039,826, which describes including shellac or other naturally-occurring film-forming polymers in sprayable sunscreens. See, also, U.S. 2010/0297043, which describes including shellac in compositions adapted to form durable, waterproof, flexible films on the surface of the skin for use as a bandage, artificial skin or protective barrier to protect the skin against contact with dirt and fluids discharged from the wearer's body such as urine, fecal mater and vomit.

These compositions are alcohol based in the sense that the external phase of the composition is ethanol or other low molecular weight (e.g., $C_1$-$C_6$) alcohol. In this context, "alcohol" will be understood to include polyols such as ethylene glycol, propylene glycol, glycerol and the like. In addition, "external phase" will be understood to mean, in the case of a solution, the solvent of the solution in which all the other ingredients are dissolved. Meanwhile, in the case of a suspension, dispersion or emulsion, the "external phase" will be understood to mean the continuous phase of the composition in which all of the ingredients not soluble in this continuous phase are either suspended, dispersed or emulsified. Normally, the majority of these alcohol-based compositions, or at least a substantial majority of the liquid in these alcohol-based compositions, is ethanol or analog.

The inventive moisturizing compositions differ from these compositions in that the inventive moisturizing compositions are water-based in the sense that the liquid forming the external (continuous) phase of the composition is water. The practical effect of this difference is at least three.

First, the substantial amount of ethanol or analog in these earlier alcohol-based compositions promotes drying of the skin, which is the exact opposite of the effect sought by a moisturizing composition, i.e., retaining skin moisture. The inventive moisturizing compositions avoid this effect, because they are water-based in the sense that they do not contain substantial amounts of ethanol or analog. This is not to say that the inventive moisturizing compositions must be entirely free of ethanol or analog. Only that the inventive compositions do not contain the large amounts of ethanol found in these earlier compositions. So, for example, the inventive moisturizing compositions may contain ethanol or other low molecular weight alcohol in amounts which are desirably no more than about 11 wt. %, more desirably no more than about 5 wt. %, no more than about 3 wt. % or even no more than about 1 wt. %, based on the weight of the inventive moisturizing compositions as whole (excluding propellant, if any).

Second, the protective films formed by the inventive moisturizing compositions exhibit a different tactile sensation or "feel" than that provided by these earlier shellac-containing compositions. This is because the protective films formed when the inventive moisturizing compositions dry are water-sensitive and hence can "breath" in the sense that they do not block moisture from evaporating from the skin. The protective films form by these earlier compositions are generally impervious to skin moisture, since they are made from water-insoluble ingredients.

Third, the shellac or analog used in the inventive moisturizing compositions is different from the shellac used in these earlier alcohol-based compositions. As well understood in the art, although shellac is soluble in ethanol and other low molecular weight alcohols, it is insoluble in water at neutral and acidic pH levels. In the earlier alcohol-based compositions mentioned above, this is of no concern as the continuous phase of the compositions is ethanol or analog. In the inventive moisturizing compositions, however, the continuous phase of the composition is aqueous. As a result a different form of shellac must be used, i.e., a water-soluble shellac.

The amount of water that is included in the inventive water-based moisturizing compositions can vary widely and depends, among other things, on the form of the composition to be made. That is to say, the amount of water in the inventive water-based moisturizing compositions depends, among other things, on whether the composition is to be made in the form of a lotion, cream, gel or sprayable composition.

For example, the inventive water-based moisturizing compositions, when made in the form of a lotion, will typically contain about 45 to 80 wt. %, more typically about 50 to 70 wt. %, or even about 55 to 65 wt. % water.

Determining the amount of water to include in particular embodiments of the inventive moisturizing compositions when made in other forms can easily be done using routine experimentation in accordance conventional practice.

Skin Care Ingredients

As indicated above, moisturizing compositions are a well-known class of materials which contain a wide variety of different ingredients designed to make the external layers of the skin (epidermis) softer and more pliable. Specific examples of these beneficial skin car ingredients include naturally occurring skin lipids and sterols, natural and/or artificial oils, humectants, emollients, lubricants and so forth. Any and all of these beneficial skin car ingredients can be included in the water-based moisturizing compositions of this invention.

For example, the inventive moisturizing compositions can contain one or more emollients, i.e., fats and oils (lipids) which are essentially water-insoluble. For example, both animal and vegetable products which contain significant quantities of stearic and palmitic acids can be used, although vegetable based products are preferred. Coconut oil and palm kernel oil are good examples of such vegetable based products, while animal fat and tallow are good examples of such animal based products. Petroleum-based emollients such as petroleum jelly and mineral oil can also be used, as can silicone oils such as cyclomethicone, dimethicone and so forth.

Of significant interest are oils that contain high levels of essential fatty acids, such as linoleic acid, since they are prized for their ability to replenish lipids (oils) that are found naturally within the skin layers. Long-chain alcohols, i.e., fatty alcohols, are also useful, as are esters of fatty alcohols and fatty acids.

Lanolin has been used for centuries due to its unique composition of complex, fatty alcohols, fatty acids and sterols such as cholesterol.

Particular emollients that can be used are fatty acids such as oleic and recinoleic; fatty alcohols such as oleyl, lauryl, and hexadecyl (ENJAY); esters such as diisopropyl adipate, benzoic acid esters of $C_9$-$C_{15}$ alcohols, and isononyl isononanoate; alkanes such as mineral oil; alkenes such as polybutenes; silicones; such as dimethylpolysiloxane and methyl phenyl polysiloxane and ethers such as polyoxypropylene butyl ethers and polyoxpropylene cetyl ethers. The most preferred water-insoluble liquid emollients are polybutene 30 cst., methyl phenyl polysiloxane, dimethylpolysiloxane 5.0 est. and polyoxypropylene (14) butyl ether.

Another type of beneficial skin care ingredient that can be included in the inventive water-based moisturizing compositions is a moisturizer. The main distinction between moisturizers and emollients is that moisturizers provide moisturizing properties but may also affect feel and sensorial attributes too. In contrast, emollients affect feel and sensorial attributes but may also provide moisturizing properties too. So, generally speaking, there is a significant overlap between the two with the overlap being greater than the difference. In general, moisturizers are soluble in water, whereas emollients are not. Moisturizers are generally polar materials that are hygroscopic in nature. Glycerin is a very cost-effective moisturizer. Sorbitol, sucrose, glucose, and other sugars are also commonly used for this purpose. Aloe, which contains a mixture of polysaccharides, carbohydrates, and minerals, is also an excellent moisturizer.

Still another type of beneficial skin care ingredient that can be included in the inventive water-based moisturizing compositions is wax. Waxes are composed primarily of long-chain esters or hydrocarbons that are solid at room temperature. Some common waxes used in cosmetics are beeswax, candelilla, carnauba, polyethylene, and paraffin. The melting points of waxes vary widely depending on their unique composition and chain lengths. By combining waxes with different properties such as high shine, flexibility, and brittleness, optimal cosmetic performance can be achieved. Often waxes are combined with compatible oils to achieve the desired softness. Waxes are particularly useful in hand creams and mascara emulsions for their emolliency, thickening and waterproofing properties.

Yet another type of beneficial skin care ingredient that can be included in the inventive water-based moisturizing compositions is a humectant. Humectants are hygroscopic substances which help keep skin moist due to their hygroscopic properties.

Specific examples of humectants that can be used to make the inventive water-based moisturizing compositions include various glycols such as propylene glycol (E1520), hexylene glycol, and butylene glycol, glyceryl triacetate (E1518), vinyl alcohol, propane diol, neoagarobiose, sugar alcohols/sugar polyols, glycerol/glycerin, sorbitol (E420), xylitol, maltitol (E965), polymeric polyols such as polydextrose (E1200), quillaia (E999), urea, aloe vera gel, MP Diol, alpha hydroxy acids (e.g., lactic acid) and honey.

Stability and Rheology Ingredients

In addition to the above beneficial skin care ingredients, the inventive water-based moisturizing compositions can also contain ingredients which serve to stabilize the composition as well as help achieve a desired viscosity. In this regard, it is well known in industry to include emulsifiers in various types cosmetics including water-based moisturizing compositions for stabilizing purposes. In addition, it is also well known to include thickeners in such compositions for rheology control, i.e., to achieve a desired viscosity. In accordance with this invention, any emulsifier as well as any thickener which has previously been used, or which may be used in the future, in water-based skin care compositions can be used in the water-based skin care compositions of this invention.

For example, all types of emulsifiers including cationic, anionic, non-ionic and amphoteric surfactants can be used for this purpose. Of particular interest are $C_{16}$-$C_{18}$ fatty acids, such as stearic acid, $C_{16}$-$C_{18}$ alcohols such as cetearyl alcohol, various glyceryl esters such as glyceryl monostearate and glyceryl distearate, and fatty acid esters of polyethylene glycol.

Similarly, all types of thickeners can be used including cellulose, Carbomers (a polyacrylic acid polymer), bentonite clays, carrageenan, pectin, xanthan gum, various types of waxes such as candelilla wax, and locust bean gum, for example.

Pharmacologically Active Ingredients

In addition to the above ingredients, the inventive water-based moisturizing compositions can also contain pharmacologically active ingredients as well. For example, these compositions can contain sunscreens, anti-acne agents, anti-wrinkle and anti-skin atrophy agents, non-steroidal anti-inflammatory actives, topical anesthetics, artificial tanning agents and accelerators, anti-microbial and antifungal actives, and various transdermal medicaments such as birth control medications, anti-smoking medications, and the like, as well as any other ingredient which is conventionally included in similar compositions.

Hedonic and Preservative Ingredients

In addition to the above ingredients, the inventive water-based moisturizing compositions can also contain still additional ingredients that are commonly included in cosmetic compositions to improve their desirability as well as for preservation purposes. For example, these compositions can include pigments, dyes, perfumes, deodorant compounds, astringent salts, antioxidants, preservatives such as biocides and fungicides, insect repellants and so forth.

Shellac Film Former

In accordance with this invention, a small but suitable amount of shellac is included in the inventive water-based moisturizing compositions, as it has been found that the presence of this ingredient improves the moisturizing effects they provide both in terms of electroconductivity as well as transdermal water loss. Bleached shellac, especially refined (i.e., dewaxed) bleached shellac, is preferred.

Shellac is a naturally occurring thermoplastic obtained from secretions of the female lac bug. It exhibits a remarkable combination of properties including low permeabilities to oxygen, water vapor, $CO_2$, ethylene and various odors, low lipid solubility, excellent color and excellent clarity.

Shellac is obtained from seedlac, an insect secretion, by removing debris from the seedlac and then further processing the seedlac to obtain the desired product. Commercially, shellac is available in two different types, bleached shellac and orange shellac. Moreover, both of these shellacs are available in refined (i.e., dewaxed) as well as unrefined (regular) versions. In addition, each of these four different varieties of shellac are available in different physical forms, e.g., solid flakes and aqueous and/or alcohol solutions. In addition, some of these different varieties are also available in different grades. For example, dewaxed orange shellac is available in a variety of different grades ranging from faint orange to intense orangish red.

As described in U.S. Pat. No. 6,348,217, the entire disclosure of which is incorporated herein by reference, bleached shellac is made by dissolving seedlac in aqueous alkali and then adding a bleaching agent such as sodium hypochlorite. The product so obtained is then precipitated and dried to produce regular bleached shellac. Alternatively, the dissolved bleached shellac can be refined by known techniques to remove its wax content before precipitating and drying, thereby producing dewaxed bleached shellac. In contrast, regular orange shellac is made by melting seedlac, sieving out the insolubles and then solidifying and flaking the product so obtained. Meanwhile, dewaxed orange shellac is made by dissolving the seedlac in alcohol, straining out the insolubles, filtering out wax particles and passing the solution so obtained through activated carbon to decolorize before solidifying and flaking. In accordance with this invention, each of these different types of shellac can be used in the inventive water-based moisturizing compositions.

As indicated above, shellac is readily soluble in alcohol, especially ethanol. However, it is essentially insoluble in water of neutral pH, although it is soluble in water having an alkaline pH.

In accordance with this invention, a water-soluble shellac is incorporated into a water-based moisturizing composition in such a way so that it is dissolved in the continuous, aqueous phase of the composition.

One especially convenient way this can be done is to dissolve the shellac into a small amount of ethanol or other low molecular weight liquid water-soluble alcohol and then combine the shellac solution so formed with a similar amount of alkaline water, with stirring. In this context, a low molecular weight liquid water-soluble alcohol will be understood to mean a $C_1$-$C_6$ alcohol containing 1 to 5 hydroxyl groups. $C_2$-$C_6$ polyols containing 2 to 5 hydroxyl groups are preferred. Similarly, a "similar" amount of water means that the weight ratio of the shellac solution to alkaline water is desirably between about 0.75:1 to 2:1, more desirably between about 1:1 to 1.7:1, or even about 1.25:1 to 1.5:1.

For example, solid, flake shellac can be slowly sprinkled into approximately twice as much liquid alcohol on a weight basis heated to 75-80° C. with stirring. Once the shellac is completely dissolved, the shellac solution so formed can then be added to approximately the same amount or slightly less of alkaline water at a pH of about 7.5-8, also maintained at about 75-80° C. with stirring. The composition so formed is then stirred until an aqueous solution containing the shellac and alcohol is obtained. Thereafter, the composition can be allowed to cool to about 50 to 60° C., after which it is then combined with the remaining ingredients of the composition, which have already been previously combined. If necessary, the pH of the final composition can be further adjusted to reach a final target pH of about 7.5 to 8.

It will therefore be appreciated that one convenient way to make the water-based moisturizing compositions of this invention is start with a previously-made (i.e., pre-existing) water in oil moisturizing composition and then add an aqueous solution containing a water-soluble shellac dissolved therein.

Alternatively, the shellac solution can be added to one or more of the ingredients forming the inventive the inventive water-based moisturizing composition prior to their combining with the other ingredients.

Regardless of the particular way the inventive moisturizing compositions are made, the amount of shellac in these compositions will normally be about 1-20 wt. %, based on the weight of the composition as a whole (excluding propellant, as mentioned above). Desirably, the amount of shellac dissolved in these compositions will be about 2 to 15 wt. %, about 3 to 10 wt. % or even 4 to 7 wt. %.

Shellac Analogs

In addition to or in lieu of shellac, any other material which is soluble in both ethanol and water at a slightly alkaline pH (i.e., pH±>7 to ~8.5) and which dries from an ethanol/water solution to form a film can be used to provide improved moisturizing properties to the water-based moisturizing compositions of this invention.

Ingredient Proportions

The relative amounts of most ingredients in the inventive water-based moisturizing compositions are conventional, and any conventional amounts can be used. Thus, the amounts of water, emollients, moisturizers, waxes, humectants, emulsifiers, thickeners, and other optional ingredients are conventional, and any conventional amount can be used for each of these ingredients.

For example, the inventive water-based moisturizing compositions can contain
- about 5 to 40 wt. %, more typically about 10 to 30 wt. %, or even about 10 to 20 wt. %, emollients,
- about 0 to 5 wt. %, more typically about 0.5 to 4 wt. %, or even about 1 to 3 wt. %, moisturizers,
- about 0 to 10 wt %, more typically about 1 to 8 wt. %, or even about 2 to 5 wt. %, humectants,
- about 0 to 15 wt. %, more typically about 1 to 10 wt. %, or even about 3 to 8 wt. %, surfactants, and
- about 0 to 5 wt. %, more typically about 0 to 3 wt. %, or even about 0.5 to 2 wt. %, thickeners, if desired.

The amount of water-soluble shellac or analog that is included in the inventive water-based moisturizing compositions should be sufficient to impart a noticeable improvement in its moisturizing properties, as reflected by the above-noted electroconductivity and transdermal water loss tests. In general this means that the amount of shellac in these composition should be about 5 to 40 wt. %, based on the combined total of all "active" ingredients in the composition including the shellac. In this context, "active ingredients" will be) understood to exclude all carrier liquids such as the alcohol which is used to dissolve the shellac as well as all water that is present (including any water that might be present in the aqueous alkaline and/or aqueous acidic solutions used to make the compositions) but to include all other ingredients in the composition even if they are present in liquid form such as a glycerin moisturizer. More desirably, the amount of water-soluble shellac in the inventive water-based moisturizing compositions is about 10 to 30, 15 to 25 wt. % or even 17 to 23 wt. % on this basis.

Examples

In order to more thoroughly illustrate this invention, the following working example is presented.

A water-based moisturizing lotion made in accordance with this invention ("product composition") was prepared in the following manner. Unless otherwise indicated, all concentrations given below are based on the total weight of this product composition.

A conventional water-based pre-existing moisturizing lotion was first made by separately preparing an organic phase and an aqueous phase and then combining the two together. The aqueous phase contained about 50 wt. % water as well as about 1 wt. % of a xanthan gum (thickener) and about 3 wt. % glycerin (humectant), while the organic phase contained a total of about 10 wt. % of three different conventional emollients, about 2 wt. % of a conventional emulsifier and about 1 wt. % of a wax thickener. The aqueous phase was vigorously mixed at 75° C. until the xanthan gum and glycerin were fully dissolved in the water of the aqueous phase, while the organic phase was similarly vigorously mixed at 75° C. until a uniform composition was obtained.

Then, the organic and aqueous phases were combined with continued vigorous mixing while maintaining the temperature at 75° C. for 5 minutes, after which the composition so obtained was homogenized by intense mixing at 3500 rpm for an additional 3 minutes. The homogenized composition so obtained was then allowed to cool to 55° C. with continued gentle mixing, thereby producing the conventional water-based moisturizing lotion.

Meanwhile, a water-soluble shellac fortifier for addition to the above conventional water-based moisturizing lotion was prepared in the following manner: About 5 wt. % of solid, flaked, refined bleached shellac was slowly added to about 11 wt. % of a short chain liquid polyol maintained at 75-80° C. with gentle agitation until the shellac had completely dissolved, thereby forming a dark brown, transparent liquid. This organic shellac solution was then slowly mixed with about 11.6 wt. % water, also maintained at 75-80° C., whose pH had previously been adjusted to about 7.5 to 8 with NaOH. Mixing was continued until the shellac and polyol were completely dissolved in the water, after which the shellac solution so obtained was allowed to cool to about 55° C.

The shellac fortifier so obtained was then added to the previously formed conventional water-based moisturizing composition with continued gentle mixing at about 55° C. until a homogenous mixture was formed, after which the composition was allowed to cool to about 40° C. About 1 wt. % benzyl alcohol (preservative) was then added, after which the composition was allowed to cool to room temperature with continued gentle mixing, thereby producing the product water-based moisturizing lotion of this invention.

This product water-based moisturizing lotion was then subjected to a standard electroconductivity test as well as a standard transdermal water loss test by applying the composition to the arm of a test subject and then measuring the results obtained Electroconductivity was measured using a Nova Dermal Phase Meter, Model DPM 9003, available from Nova Technology Corporation of Gloucester, Mass., while transdermal water loss test was measured using a DermaLab Computerized Evaporimeter, available from Cyberderm, Inc. of Broomall, Pa.

Each test was separate run on two different test subjects, Subject A and Subject B. In addition, for purposes of comparison, identical tests were carried out on the bare (untreated) skin of the other arm of each individual. Readings were taken at the start of each test (in the case of the inventive water-based moisturizing lotion, immediately after it was applied) as well as periodically thereafter, Average values were then determined and then normalized to provide accurate comparisons. The difference between the normalized value at time zero and the normalized values obtained at each subsequent measurement was then determined, thereby providing a measure of the effectiveness of the inventive water-based composition in improving skin moisturizing.

The results obtained are set forth in the following Tables 1 and 2:

TABLE 1

Moisturization Study
Skin Surface Electroconductivity

|  | Untreated Skin | | | | Inventive Moisturizing Composition | | | |
| --- | --- | --- | --- | --- | --- | --- | --- | --- |
|  | 0 min | 15 min | 30 min | 60 min | 0 min | 15 min | 30 min | 60 min |
| Sub A | 97.33 | 97.33 | 97.33 | 97.33 | 98.67 | 198.00 | 180.00 | 157.33 |
| Sub B | 103.33 | 104.67 | 104.00 | 104.67 | 106.67 | 212.67 | 200.00 | 170.00 |
| Average | 100.33 | 101.00 | 100.67 | 101.00 | 102.67 | 205.34 | 190.00 | 163.67 |
| Normal | 101.50 | 102.18 | 101.84 | 102.18 | 101.50 | 203.00 | 187.83 | 161.80 |
| Difference |  | 0.67% | 0.33% | 0.67% |  | 100.00% | 85.06% | 59.41% |

TABLE 2

Moisturization Study
Transepidermal Water Loss (TEWL)

|  | Untreated Skin | | | | Inventive Moisturizing Composition | | | |
| --- | --- | --- | --- | --- | --- | --- | --- | --- |
|  | 0 min | 15 min | 30 min | 60 min | 0 min | 15 min | 30 min | 60 min |
| Sub A | 4.26 | 4.20 | 3.96 | 3.80 | 4.06 | 3.02 | 2.50 | 2.73 |
| Sub B | 5.02 | 4.97 | 5.15 | 5.23 | 4.19 | 2.86 | 2.42 | 2.43 |
| Average | 4.64 | 4.59 | 4.56 | 4.52 | 4.13 | 2.94 | 2.46 | 2.58 |
| Normal | 4.38 | 4.33 | 4.30 | 4.26 | 4.38 | 3.12 | 2.61 | 2.74 |
| Difference |  | −1.14% | −1.83% | −2.74% |  | −28.77% | −40.41% | −37.44% |

From Table 1, it can be seen that the electroconductivity of the untreated skin of the test subjects remained essentially unchanged over the entire one hour testing period. On the other hand, the electroconductivity of the skin treated with the inventive water-based moisturizing lotion doubled (increased by 100%) immediately after it was applied, with this substantial increase in surface impedance then slowly decreasing over time.

Similarly, Table 2 shows that the transdermal water loss of the untreated skin of the test subjects remained essentially unchanged over the entire one hour testing period, while the transdermal water loss of the skin treated with the inventive water-based moisturizing lotion decreased substantially relative to the untreated skin during the entire one hour test period.

Together, these tests show that the inventive water-based moisturizing composition provides a substantial increase in skin moisturization relative to untreated skin.

Although only a few embodiments of this invention have been described above, it should be appreciated that many modifications can be made without departing from the spirit and scope of this invention. All such modifications are intended to be included within the scope of this invention, which is to be limited only by the following claims:

The invention claimed is:

1. A water-based skin moisturizing composition in the form of oil-in-water emulsion, comprising an aqueous phase and an oil phase emulsified in the aqueous phase, wherein the oil phase comprises one or more emollients,
   wherein a water-soluble shellac is dissolved in the aqueous phase in an amount sufficient to improve the moisturizing properties of the emulsion,
   wherein the amount of the water-soluble shellac is from 1 to 20 wt. % based on the emulsion as a whole,
   wherein the emulsion contains about 45 to 80 wt. % water based on the emulsion as a whole,
   wherein the amount of water-soluble low molecular alcohols containing 1 to 6 carbons atoms and 1 to 5 hydroxyl groups in the composition, if any, is less than the amount of water in the composition,
   wherein the emulsion has an alkaline pH, and
   wherein the composition is in the form of a lotion, paste, cream or gel.

2. The skin moisturizing composition of claim 1, wherein the composition contains no more than about 11 wt. % of water-soluble low molecular alcohols containing 1 to 6 carbons atoms and 1 to 5 hydroxyl groups.

3. The skin moisturizing composition of claim 2, wherein the composition contains no more than about 5 wt. % of water-soluble low molecular alcohols containing 1 to 6 carbons atoms and 1 to 5 hydroxyl groups.

4. The skin moisturizing composition of claim 3, wherein the composition has a pH of >7 to about 8.5.

5. The skin moisturizing composition of claim 4, wherein the composition has a pH of about 7.5 to 8.

6. The skin moisturizing composition of claim 2, wherein the composition has a pH of >7 to about 8.5.

7. The skin moisturizing composition of claim 6, wherein the composition has a pH of about 7.5 to 8.

8. The skin moisturizing composition of claim 1, wherein the concentration of water-soluble shellac in the composition is about 2-15 wt. % based on the composition as a whole.

9. The skin moisturizing composition of claim 1, wherein the concentration of water-soluble shellac in the composition is about 5 to 40 wt. %, this wt. % being based on all of the ingredients in the composition excluding the water and any alcohol that might be present.

10. The skin moisturizing composition of claim 1, wherein the composition contains one or more water-soluble low molecular weight alcohols containing 1 to 6 carbon atoms and 1 to 5 hydroxyl groups.

11. The skin moisturizing composition of claim 1, wherein the composition is in the form of a lotion and further wherein the composition contains about 45 to 80 wt. % water based on the composition as a whole.

12. The skin moisturizing composition of claim 11, wherein the composition contains about 2 to 15 wt. % water-soluble shellac and 50 to 70 wt. % water based on the composition as a whole.

13. The skin moisturizing composition of claim 1, wherein the water-soluble shellac is dewaxed shellac.

14. The skin moisturizing composition of claim 13, wherein the water-soluble shellac is dewaxed bleached shellac.

15. The skin moisturizing composition of claim 1, wherein the composition is made by combining one or more ingredients of the composition with a pre-formed fortifying mixture comprising shellac dissolved in a mixture of water having an alkaline pH and one or more water-soluble low molecular weight alcohols containing 1 to 6 carbon atoms and 1 to 5 hydroxyl groups.

16. A water-based skin moisturizing composition in the form of oil-in-water emulsion, comprising an aqueous phase and an oil phase emulsified in the aqueous phase,
   wherein the oil phase comprises one or more emollients,
   wherein a water-soluble shellac which is water-soluble because it is in contact with alkaline water is dissolved in the aqueous phase in an amount sufficient to improve the moisturizing properties of the emulsion,
   wherein the amount of the water-soluble shellac is from 1 to 20 wt. % based on the emulsion as a whole,
   wherein the emulsion contains about 45 to 80 wt. % water based on the emulsion as a whole,
   wherein the composition contains no more than about 11 wt. % of water-soluble low molecular alcohols containing 1 to 6 carbons atoms and 1 to 5 hydroxyl group, and
   wherein the composition is in the form of a lotion, paste, cream or gel.

17. A water-based skin moisturizing composition in the form of oil-in-water emulsion, comprising an aqueous phase and an oil phase emulsified in the aqueous phase,
   wherein the oil phase comprises one or more emollients,
   wherein a water-soluble shellac is dissolved in the aqueous phase in an amount sufficient to improve the moisturizing properties of the emulsion,
   wherein the amount of the water soluble shellac is from 1 to 20 wt. % based on the emulsion as a whole,
   wherein the emulsion contains about 45 to 80 wt. % water based on the emulsion as a whole,
   wherein the emulsion contains not more than 5 wt. % of water-soluble low molecular alcohols containing 1 to 6 carbons atoms and 1 to 5 hydroxyl groups,
   wherein the emulsion has a pH of about 7.5 to 8, and
   wherein the composition is in the form of a lotion, paste, cream or gel.

* * * * *